US008550973B2

(12) United States Patent
Magovern et al.

(10) Patent No.: US 8,550,973 B2
(45) Date of Patent: Oct. 8, 2013

(54) PERCUTANEOUS RIGHT VENTRICULAR ASSIST APPARATUS AND METHOD

(75) Inventors: James A. Magovern, Pittsburgh, PA (US); Scott B. Allison, Salt Lake City, UT (US); Royce G. Barraclough, Kaysville, UT (US); James R. Revenaugh, Salt Lake City, UT (US); Douglas E. Smith, Pittsburgh, PA (US); David H. J. Wang, Pittsburgh, PA (US)

(73) Assignee: CardiacAssist, Inc., Pittsburgh, PA (US)

( * ) Notice: Subject to any disclaimer, the term of this patent is extended or adjusted under 35 U.S.C. 154(b) by 1177 days.

(21) Appl. No.: 11/328,961

(22) Filed: Jan. 9, 2006

(65) Prior Publication Data

US 2007/0161845 A1 Jul. 12, 2007

(51) Int. Cl.
*A61N 1/362* (2006.01)

(52) U.S. Cl.
USPC .................................. 600/16; 600/17; 600/18

(58) Field of Classification Search
USPC ............................................. 600/16, 17, 18
See application file for complete search history.

(56) References Cited

U.S. PATENT DOCUMENTS

| 3,152,340 | A |   | 10/1964 | Fry et al. |
|-----------|---|---|---------|------------|
| 3,884,808 | A |   | 5/1975  | Scott |
| 4,573,997 | A | * | 3/1986  | Wisman et al. ............... 623/3.16 |
| 4,871,358 | A | * | 10/1989 | Gold ............................. 604/271 |
| 4,927,407 | A |   | 5/1990  | Dorman |
| 4,994,027 | A |   | 2/1991  | Farrell |
| 5,044,897 | A |   | 9/1991  | Dorman |
| 5,079,467 | A |   | 1/1992  | Dorman |
| 5,171,218 | A |   | 12/1992 | Fonger et al. |
| 5,190,528 | A |   | 3/1993  | Fonger et al. |
| 5,308,319 | A |   | 5/1994  | Ide et al. |
| 5,314,418 | A |   | 5/1994  | Takano et al. |
| 5,330,433 | A |   | 7/1994  | Fonger et al. |
| 5,376,114 | A |   | 12/1994 | Jarvik |
| 5,449,342 | A |   | 9/1995  | Hirose et al. |
| 5,599,306 | A |   | 2/1997  | Klein et al. |

(Continued)

OTHER PUBLICATIONS

Frazier et al., "First Clinical Use of the Redesigned HeartMate(trademarked) II Left Ventricular Assist System in the United States: a Case Report." Texas Heart Institute Journal vol. 31, No. 2, 2004; pp. 157-159.*

(Continued)

*Primary Examiner* — Niketa Patel
*Assistant Examiner* — William Levicky
(74) *Attorney, Agent, or Firm* — The Webb Law Firm

(57) ABSTRACT

A system for assisting the right heart of a patient includes a PA cannula adapted for insertion into a PA of a patient through the right internal jugular vein of the patient. The system includes a percutaneous RA cannula adapted for insertion into an RA of the patient. The system includes a blood pump disposed outside of the patient to which the RA cannula and the PA cannula are connected to provide right ventricular circulatory support to the patient without any left ventricular assist. A method for assisting the right heart of a patient includes the steps of inserting a PA cannula into a PA of a patient. There is the step of inserting an RA cannula into an RA of the patient. There is the step of connecting the RA cannula and the PA cannula to a blood pump disposed outside of the patient. There is the step of activating the blood pump to provide right ventricular circulatory support to assist the heart of the patient.

20 Claims, 5 Drawing Sheets

(56) References Cited

U.S. PATENT DOCUMENTS

| | | | |
|---|---|---|---|
| 5,711,753 A | 1/1998 | Pacella et al. | |
| 5,810,758 A | 9/1998 | Yamazaki et al. | |
| 5,840,070 A | 11/1998 | Wampler | |
| 5,885,238 A | 3/1999 | Stevens et al. | |
| 5,916,193 A | 6/1999 | Stevens et al. | |
| 5,928,181 A | 7/1999 | Coleman et al. | |
| 5,931,829 A * | 8/1999 | Burbank et al. | 604/502 |
| 5,954,696 A | 9/1999 | Ryan | |
| 5,957,879 A | 9/1999 | Roberts et al. | |
| 6,045,496 A | 4/2000 | Pacella et al. | |
| 6,083,260 A | 7/2000 | Aboul-Hosn | |
| 6,090,096 A * | 7/2000 | St. Goar et al. | 604/509 |
| 6,110,139 A | 8/2000 | Loubser | |
| 6,135,943 A | 10/2000 | Yu et al. | |
| 6,162,167 A | 12/2000 | Goldstein et al. | |
| 6,217,546 B1 | 4/2001 | Hinchliffe et al. | |
| 6,443,884 B1 | 9/2002 | Miyawaki | |
| 6,447,441 B1 | 9/2002 | Yu et al. | |
| 6,497,698 B1 | 12/2002 | Fonger et al. | |
| 6,676,650 B1 | 1/2004 | Magovern et al. | |
| 6,685,621 B2 * | 2/2004 | Bolling et al. | 600/16 |
| 6,716,189 B1 * | 4/2004 | Jarvik et al. | 604/6.16 |
| 6,790,171 B1 * | 9/2004 | Grundeman et al. | 600/18 |
| 6,808,482 B1 | 10/2004 | Pacella et al. | |
| 6,808,508 B1 * | 10/2004 | Zafirelis et al. | 604/131 |
| 7,022,100 B1 | 4/2006 | Aboul-Hosn et al. | |
| 7,267,660 B2 | 9/2007 | Fonger et al. | |
| 2003/0208097 A1 * | 11/2003 | Aboul-Hosn et al. | 600/16 |
| 2004/0034272 A1 * | 2/2004 | Diaz et al. | 600/18 |
| 2004/0068220 A1 * | 4/2004 | Couvillon et al. | 604/6.11 |
| 2005/0004421 A1 | 1/2005 | Pacella et al. | |
| 2005/0085772 A1 | 4/2005 | Zafirelis et al. | |

OTHER PUBLICATIONS

Yano et al., "The Feasibility and Efficacy of Right Ventricular . . ." from ASAIO Journal (American Society for Artificial Internal Organs : 1992).*

Keichiro Matsuo et al. "Potentialies and Problems of a Novel Bilateral Ventricular Assist System Without Thoracotomy," Artificial Organs, Blackwell Science, Inc., (vol. 24), (Issue. 2) (p. 148-155), (2000).*

Mitsuhiro Yano, et al. "Efficacy and Safety of a Percutaneous Right Ventricular Assist System," The Society of Thoracic Surgeons, Elsevier Science, Inc., (vol. 61), (p. 1231-1235), (1996).*

Mitsuhiro Yano, et al., "The Feasibility and Efficacy of Right Ventricular Assistance without Thoracotomy," ASAIO Journal, American Society for Artificial Internal Organs, (p. 120-125), (1992).

Keiichiro Matsuo, et al., "Potentialities and Problems of a Novel Bilateral Ventricular Assist System Without Thoracotomy," Artificial Organs, Blackwell Science, Inc., (vol. 24), (Issue. 2), (p. 148-155), (2000).

Mitsuhiro Yano, et al., "Efficacy and Safety of a Percutaneous Right Ventricular Assist System," The Society of Thoracic Surgeons, Elsevier Science, Inc., (vol. 61), (p. 1231-1235), (1996).

O. H. Frazier, et al., "First Clinical Use of the Redesigned HeartMate II Left Ventricular Assist System in the United States," Texas Heart Institute Journal, Texas Heart Institute (Houston), (vol. 31), (Issue. 2), (p. 157-159), (2004).

Bruce Toporoff, et al., "Pulmonary Complications of a Roller Pump Right Ventricular Assist Device," Journal of Surgical Research, Academic Press, Inc., (vol. 45), (Issue. 1), (p. 21-27), (Jul. 1988).

Rose et al. "Technique and Results with a Roller Pump Left and Right Heart Assist Device" Annals of Thoracic Surgery. 1989. pp. 124-129. vol. 47. The Society of Thoracic Surgeons.

Babic et al. "Non-Surgical Left-Atrial Aortic Bypass" The Lancet. Dec. 17, 1988. pp. 1430-1431.

Pavie et al. "Left Centrifugal Pump Cardiac Assist with Transseptal Percutaneous Left Atrial Cannula" Artificial Organs. 1998. pp. 502-507. 22(6). International Society for Artificial Organs.

Hall et al. "An Experimental Study of Prolonged Left Heart Bypass Without Thoracotomy" Annals of Surgery. Aug. 1962. pp. 190-196. 156(2).

* cited by examiner

THE RIGHT INTERNAL JUGULAR VEIN IS PUNCTURED WITH A NEEDLE. A WIRE IS THEN ADVANCED INTO THE RIGHT ATRIUM.

AFTER DILATING THE SKIN SITE AND THE VEIN, THE 17 FR WIRE-REINFORCED CANNULA AND INTRODUCER ARE ADVANCED INTO THE RIGHT ATRIUM.

THE 17 FR CANNULA IS SHOWN IN THE RIGHT ATRIUM.

A 7 FR SWAN-GANZ CATHETER IS THEN PASSED THROUGH THE CANNULA AND FLOATED INTO THE RIGHT PULMONARY ARTERY.

A SUPER-STIFF WIRE (0.035) IS THEN PASSED THROUGH THE SWAN-GANZ CATHETER TO STIFFEN IT.

THE 17 FR CANNULA IS ADVANCED OVER THE SWAN-GANZ CATHETER UNTIL IT SITS IN THE DISTAL MAIN PULMONARY. THE SWAN-GANZ CATHETER AND THE WIRE ARE REMOVED, LEAVING THE CANNULA IN POSITION.

THE 21 FR VENOUS DRAINAGE CANNULA IS ADVANCED FROM THE FEMORAL VEIN OVER A WIRE, USING THE SELDINGER TECHNIQUE

THE 21 FR VENOUS DRAINAGE CANNULA IS POSITIONED IN THE RIGHT ATRIUM AND THE 17 FR RETURN CANNULA IS IN THE MAIN PULMONARY ARTERY.

PERCUTANEOUS RIGHT VENTRICULAR ASSIST APPARATUS AND METHOD

FIELD OF THE INVENTION

The present invention is related to right ventricular assist. More specifically, the present invention is related to right ventricular assist without any left ventricular assist and without any open chest surgery.

BACKGROUND OF THE INVENTION

Right ventricular (RV) failure is known to occur in 10-15% of patients following left ventricular assist device (LVAD) placement. In addition, acute RV failure following orthotopic cardiac transplantation is also known to occur, and may be related to RV stunning at the time of organ harvest and administration of cardioplegia. RV failure in these settings is often reversible, not requiring long term mechanical support. Currently, commercially available devices approved for RV assist involve the surgical placement of either centrifugal or pulsatile devices, all of which require surgical operation for both placement and device removal. A percutaneously placed right ventricular assist device, if available, could spare patients the risk resulting from general anesthesia and open heart operation.

The current TandemHeart PTVA system is a percutaneous left ventricular assist system comprised of a centrifugal pump, a 21 Fr, ~65 cm long uptake cannula designed to be placed across the interatrial septum using standard transseptal puncture technique, and a 15 or 17 Fr return cannula; with the cannulae connected to the pump using standard ⅜ inch surgical tubing. Systemic flow rates of 3.5-4.0 Liters/Min can be achieved. This device has been studied on acute cardiogenic shock patients and was found to confer a significant hemodynamic benefit compared to the intraaortic balloon pump (IABP). It is currently approved by the FDA for temporary (<6 hr) left ventricular mechanical circulatory support, and based on the results of the cardiogenic shock trial, will likely receive an FDA approved indication in the setting of acute cardiogenic shock due to left heart failure.

There are three previous publications on the topic of percutaneous right ventricular assistance. Two are by Yano (Trans Am Soc Artif Organs 1993; 39:120-25, Ann Thorac Surg 1996; 61:1231-35). These report on the same work, one preliminary and the other with more data. The third is from Matsuo with Yano as the second author (Artif Organs 2000; 24:148-55). This is from the same group and is very similar to the other two reports.

These papers report the results of right ventricular assistance in experimental animals, using custom designed cannulae and off the shelf centrifugal pumps. The cannulae are prototypes and not available on the commercial market. The pumps are commercially available devices, typically used for cardiopulmonary bypass. These pumps are for short-term use during surgery and should not be considered as ventricular assist devices. In all of the experiments, the right-side assistance was used in conjunction with left side support. The original paper was in 1993 and it has not been applied in a patient by this group.

SUMMARY OF THE INVENTION

The present invention pertains to a system for assisting the right heart of a patient. The system comprises a PA (Pulmonary Artery) cannula adapted for insertion into a PA of a patient through the right internal jugular (RIJ) vein of the patient. The system comprises a percutaneous RA cannula adapted for insertion into an RA (Right Atrium) of the patient. The system comprises a blood pump disposed outside of the patient to which the RA cannula and the PA cannula are connected to provide right ventricular circulatory support to the patient without any left ventricular assist.

The present invention pertains to a method for assisting the right heart of a patient. The method comprises the step of inserting a PA cannula into a PA of a patient. There is the step of inserting an RA cannula into an RA of the patient. There is the step of connecting the RA cannula and the PA cannula to a blood pump disposed outside of the patient. There is the step of activating the blood pump to provide right ventricular circulatory support to assist the heart of the patient.

The present invention provides a means of right heart support without surgery. Placement of the device is accomplished percutaneously. A percutaneous intake cannula is placed in the patient's RA via RFV (Right Femoral Vein) and is connected to a blood pump outside of the body. Blood is pumped back to the PA through an outflow cannula placed in RIJ. The right ventricle is totally bypassed. No open chest surgery is necessary.

BRIEF DESCRIPTION OF THE DRAWINGS

In the accompanying drawings, the preferred embodiment of the invention and preferred methods of practicing the invention are illustrated in which.

DETAILED DESCRIPTION

Figure 9:
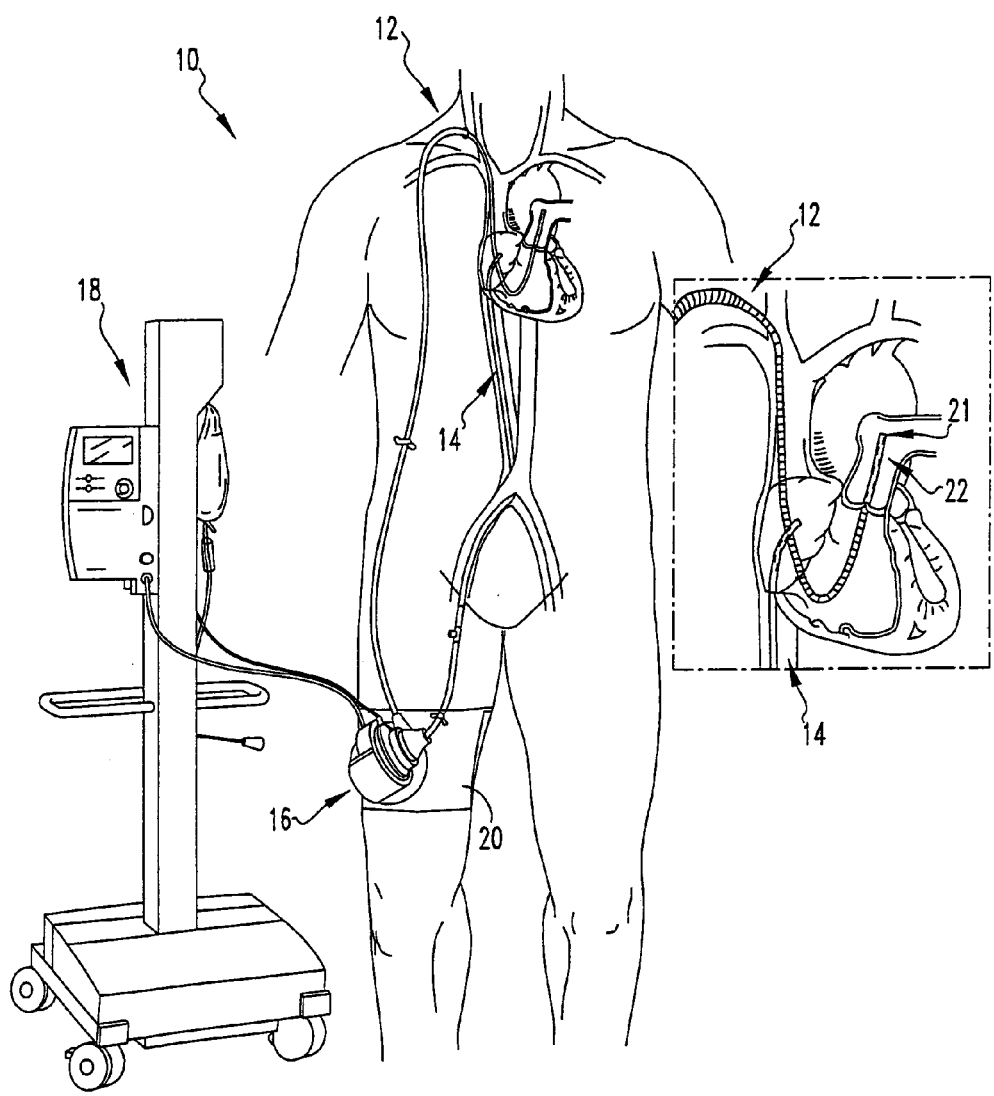
FIG. 9 is a schematic representation of the system of the present invention.

Referring now to the drawings wherein like reference numerals refer to similar or identical parts throughout the several views, and more specifically to FIG. 9 thereof, there is shown a system 10 for assisting the right heart of a patient. The system 10 comprises a PA cannula 12 adapted for insertion into a PA (pulmonary artery) of a patient through the right internal jugular vein of the patient. The system 10 comprises a percutaneous RA cannula 14 adapted for insertion into an RA of the patient. The system 10 comprises a blood pump disposed outside of the patient to which the RA cannula and the PA cannula 12 are connected to provide right ventricular circulatory support to the patient without any left ventricular assist. Preferably, the pump is a ventricular assist pump.

The present invention pertains to a method for assisting the right heart of a patient. The method comprises the steps of inserting a PA cannula 12 into a PA of a patient. There is the step of inserting an RA cannula 14 into an RA of the patient. There is the step of connecting the RA cannula 14 and the PA cannula 12 to a blood pump disposed outside of the patient. There is the step of activating the blood pump to provide right ventricular circulatory support to assist the right heart of the patient.

Preferably, the activating step includes the step of providing flow from the blood pump for right ventricular assist of the patient at a level which is ½ to ⅔ of normal cardiac output flow of the patient. The activating step preferably includes the step of providing only right ventricular assist with the blood pump to the patient without any left ventricular assist. Preferably, the inserting the PA cannula 12 step includes the step of passing a Swan-Ganz catheter through the cannula, floating it into the pulmonary artery, and advancing a super stiff wire through a pulmonary artery port of the Swan-Ganz catheter.

The PA cannula 12 preferably has an end hole 22 and at least two side holes 22 which allow blood flow to the left and right lungs of the patient, without promoting backflow into the right ventricle of the patient. Preferably, no open chest surgery occurs. The inserting the RA cannula 14 step preferably includes the step of inserting the RA cannula 14 percutaneously into the RA of the patient. Preferably, the right ventricle of the patient is totally bypassed. The activating step preferably includes the step of pumping unoxygenated blood from the right atrium with the blood pump through the percutaneous RA cannula 14 and returning the blood to the pulmonary artery through the PA cannula.

Preferably, the pumping step includes the step of controlling the pump with a controller 18 in communication with the pump which detects and manages faults and produces an alert signal in response to a detected fault. There is preferably the step of placing the pump in a holder 20 that attaches to the lower body of the patient. Preferably, there is the step of sewing the PA cannula 12 and the RA cannula 14 to the patient. The inserting the PA cannula 12 step preferably includes the step of inserting the PA cannula 12 through the right internal jugular vein of the patient. Preferably, the inserting the PA cannula 12 step includes the step of removing the Swan-Ganz catheter and the wire from the patient once the PA cannula 12 is in the patient.

The inserting the RA cannula 14 step preferably includes the step of inserting the RA cannula 14 into a peripheral vein of the patient over a long wire which has been placed in the RA using Seldinger technique. The inserting the RA cannula 14 step preferably includes the step of advancing the RA cannula 14 along the long wire into the RA and removing the long wire. Preferably, the activating step includes the step of starting 2 L/min flow for at least two minutes and then adjusting the flow based on the patient's requirements. There is preferably the step of using imaging guidance when the RA cannula 14 and the PA cannula 12 are placed in the RA and PA, respectively.

In the operation of the preferred embodiment, the system 10 comprises a blood pump, connected to a percutaneous RA cannula 14 at the pump inlet, for pumping unoxygenated blood from the right atrium through the RA cannula 14 and returning the blood to the pulmonary artery through the PA cannula. The blood pump is controlled by a controller 18 that monitors key system 10 operating parameters to detect and manage faults and to alert operators.

The pump 16 and controller 18 operation will be the same as described in U.S. Pat. No. 6,808,508, incorporated by reference herein.

Preferably, the system 10 includes a holder 20 which holds the blood pump in place. The holding mechanism preferably attaches to the patient's lower body. One important feature of the holder 20 is to maintain the position of the pump relative to the cannulae. Since the cannulae are in the patient, it is therefore a general rule that the position of the pump is maintained relative to the patient. However, the details of how that is accomplished are less important, and will depend on the cannulation sites. The possibility that the cannulae will be inadvertently pulled out of the patient, or that the cannulae will become disconnected from the pump is minimal. Either event would be a crisis. The cannulae will be sutured in place, and the pump will likewise be secured. It could be secured to the patient's leg, waist, or shoulder, for example. It could be mounted onto the patient's bed, provided that the patient is also secured to the bed. It could be mounted on a rail or pole, which in turn is attached to the bed, as is the patient.

Other features that need to be kept in mind are prime volume and pressure drop. It is desired to mount the pump in a holster on the patient so that the connecting tubing can be maintained as short as possible, thus minimizing the prime volume to about 100 cc, and keeping pressure drop as low as possible (thus maximizing flow rate). If one cannula is in the leg and one is in the neck, it will be important to provide a means of connecting the two with a circuit as compact as possible. So a pump placed on the leg, waist or shoulder could provide a very short path to one cannula and a long path to the other, or equal path lengths to both cannulae. In any case, the advantage of fixing the pump in a securing and stabilizing means also allows the connecting tubing to be arranged in a compact circuit. In terms of pressure drops, it will be advantageous to minimize the negative pressure drop (very high negative pressure can lead to hemolysis or cavitation in the blood), so it will usually be best to locate the pump close to the cannula which takes blood from the patient's right atrium/SVC (Superior Vena Cava)/IVC (Interior Vena Cava) and carries it to the pump. The longer tubing run can then be on the outflow side, which is the positive pressure side of the pump. If femoral cannulation is used to access the RA, the pump holster and location described in U.S. Pat. No. 6,808,508, incorporated by reference herein, would work quite well.

To minimize circuit volume and pressure drop, and also to maximize patient mobility (for bathing, changing dressings, etc.), it may be advantageous to locate both the cannulae in the neck or the upper part of the body. The patient's shoulder can then be used as a mounting location for the pump. This also has the advantage of leaving the groin open and accessible for percutaneous LVAD access, interventional cardiology access, or other needs.

The RA cannula 14 Set includes:

1 17 or 21 Fr percutaneous RA Cannula 1 14 Fr Percutaneous RA cannula 14 Introducer The following instruments are needed to complete the procedure and should be supplied by the user (all the standard in art)

Introducer needle

Vessel dilator

Guidewire, super stiff, 0.035, at least 150 cm long

The insertion procedure is described below.

The PA cannula 12 Set includes:

1 17 or 21 Fr percutaneous PA Cannula 1 14 Fr Percutaneous PA cannula 12 Introducer Insertion of PA cannula 12 is described below. Connecting of RA and PA to the pump is described below.

The invention consists of a system 10 for providing percutaneous right ventricular assistance for treatment of temporary and reversible right heart problems. These include right ventricular infarction, right ventricular dysfunction after heart transplantation or LVAD implantation, right ventricular distention after cardiac surgery and right ventricular dysfunction resulting from left heart valve diseases. The system 10 consists of three components: 1) a cannula placed in the right atrium from a peripheral vein (femoral, jugular, subclavian); 2) a blood pump that is also a ventricular assist device, which can pump 2-4 L/min with minimal blood trauma or clotting; and 3) a cannula placed into the pulmonary artery from a peripheral vein. This cannula must be flexible enough to make the passage through the right heart to the pulmonary artery, but stiff enough to resist kinking, which would obstruct blood flow. The cannula must also have an end-hole and at least two large side holes, which allow blood flow to the left and right lungs, without allowing backflow into the right ventricle.

The placement of the system 10 is done as follows:
1. The PA cannula 12 is inserted first so that no interference occurs from another cannula in the right atrium.
2. Heparin is given intravenously to maintain ACT level greater than 200 seconds during the placement.
3. The right internal jugular vein is punctured with a needle and accessed through a wire 23.
4. The skin site and vein are dilated.
5. The percutaneous PA cannula 12 and its introducer are advanced over the wire 23 into the right atrium, which is confirmed by fluoroscopy or echocardiography,
6. The introducer and the wire 23 are removed.
7. A pulmonary wedge pressure catheter 26 is then passed through the cannula 12 and floated into the pulmonary artery.
8. A 0.035 super stiff wire is advanced through the pulmonary wedge pressure catheter.
9. The PA cannula 12 is advanced over the pulmonary wedge pressure catheter 26 up to the inflated balloon 27.
10. The catheter 26 and the wire are removed, the balloon 27 is then deflated once proper positioning is confirmed by fluoroscopy, leaving the cannula in the PA.

If a Swan-Ganz catheter is already in place in the right internal jugular vein when the decision is made to place the RVAD, then the insertion procedure changes. In this situation, the insertion of the PA cannula 12 is as follows:
1. The Swan-Ganz catheter is removed. A wire is placed through the introducer and positioned in the PA.
2. The introducer is removed leaving the wire in the RA.
3. The percutaneous PA cannula 12 and its introducer are advanced over the wire, into the right atrium.
4. The introducer is removed, leaving the cannula in the RA.
5. A pulmonary wedge pressure catheter is passed through the cannula and floated in the pulmonary artery. A 0.035 super-stiff wire is advanced through the pulmonary wedge pressure catheter.
6. The PA cannula 12 is advanced over the Swan-Ganz catheter up to the balloon.
7. (The balloon is deflated) The Swan-Ganz catheter and the wire are removed, leaving the cannula in the pulmonary artery.

The next step is placement of the RA cannula. This is done from a peripheral vein, such as the femoral, jugular or subclavian vein. The procedure is as follows:
1. The vein is punctured with a needle and accessed through a wire.
2. The skin site and the vein are dilated with a vessel dilator.
3. The RA cannula 14 with its introducer are placed into the vein and the wire is removed.
4. A long wire 25 is passed through the RA cannula/introducer until it reaches the RA.
5. The cannula/introducer is advanced into the RA using fluoroscopic guidance.
6. The introducer and wire 25 are removed leaving the cannula 14 in the RA.

The next step is connection of the RA and PA cannula 12 to the blood pump.
1. The RA and PA cannulas are allowed to back-bleed to remove air.
2. The RA cannula 14 is connected to the inflow part of the pump and allowed to back-bleed to fill the pump with blood and displace air.
3. The RA cannula 14 is clamped with a tubing clamp.
4. The PA cannula 12 is then connected to the pump outlet, taking care to avoid air in the circuit.
5. Secure pump and system in place.
6. The clamp is removed from the RA cannula.
7. The pump is started at 2 L/min flow for 5 minutes and then increased as needed, depending on the patient's needs and the specific clinical situation.

Several clinical points are important.
1. RV Pump flow should never be excessive in order to avoid lung injury. In most circumstances, RV pump flow should be limited to 50-75% of the measured or estimated systemic cardiac output.
2. RV size and function should be examined with echocardiography before and during RV assistance to confirm RV decompression while avoiding complete RV collapse during assistance.
3. The position of the PA cannula 12 should be confirmed by chest x-ray or fluoroscopy at least once per day.
4. The right internal jugular vein is the preferred access site for the percutaneous PA cannula, because it allows an optimal anatomic pathway through the right heart and because it is the shortest route to the PA.

Figure 1:
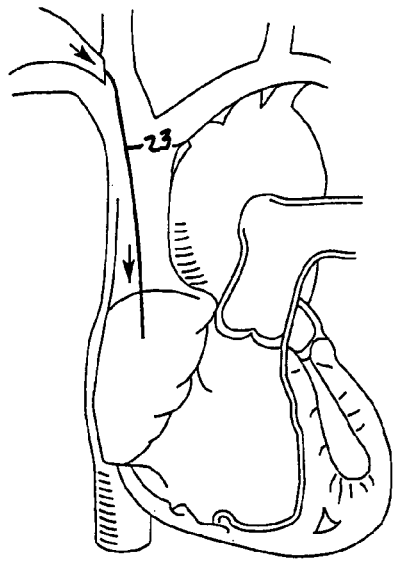
FIG. 1 is a schematic representation of a right internal jugular vein punctured with a needle. The wire is then advanced into the right atrium.
Figure 2:
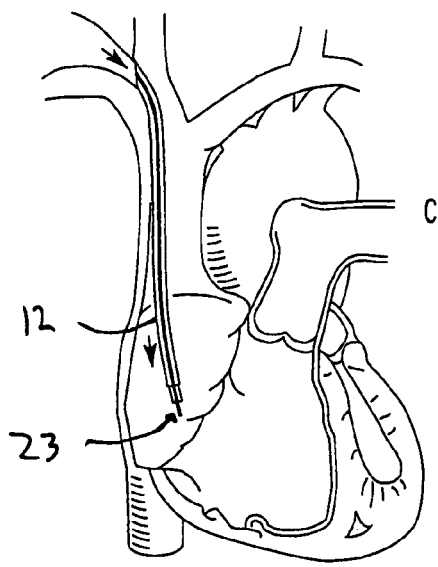
FIG. 2 is a schematic representation of a 17 Fr wire-reinforced cannula and introducer advanced into the right atrium after dilating the skin site and the vein.
Figure 3:
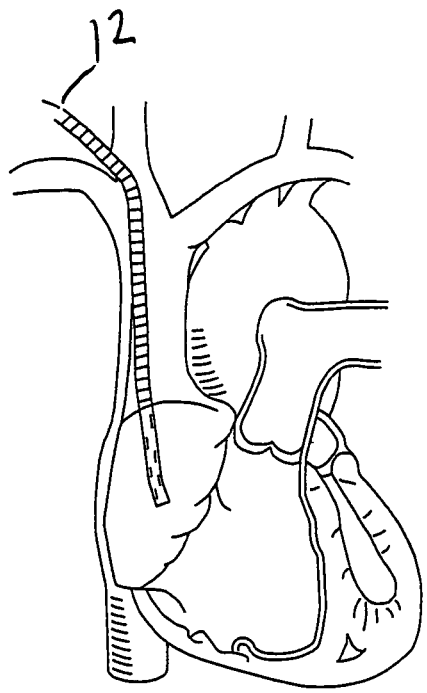
FIG. 3 is a schematic representation of the 17 Fr cannula in the right atrium.
Figure 4:
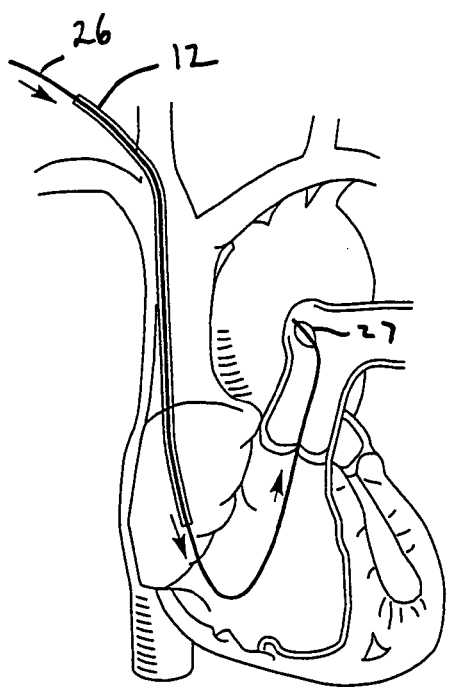
FIG. 4 is a schematic representation of a 7 Fr Swan-Ganz catheter that has passed through the cannula and floated into the right pulmonary artery.
Figure 5:
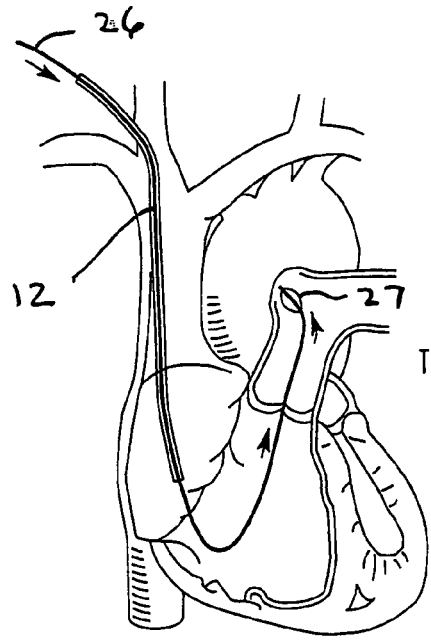
FIG. 5 is a schematic representation of a super-stiff wire passed through the Swan-Ganz catheter to stiffen it.
Figure 6:
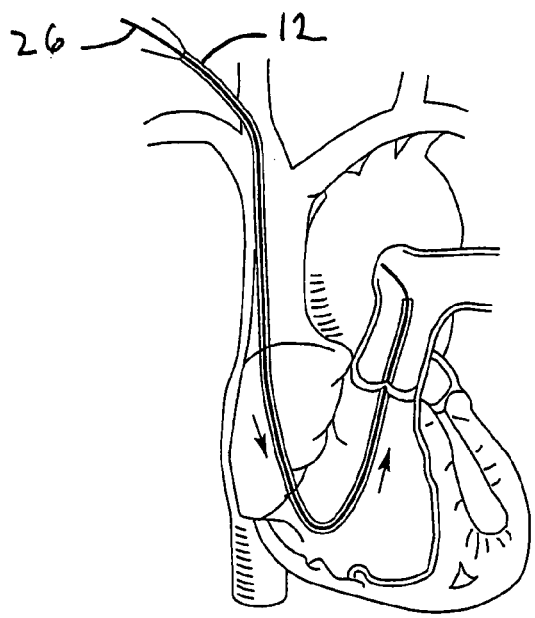
FIG. 6 is a schematic representation of the 17 Fr cannula advanced over the Swan-Ganz catheter until it sits in the distal main pulmonary artery. The Swan-Ganz catheter and the wire are removed, leaving the cannula in position.
Figure 8:
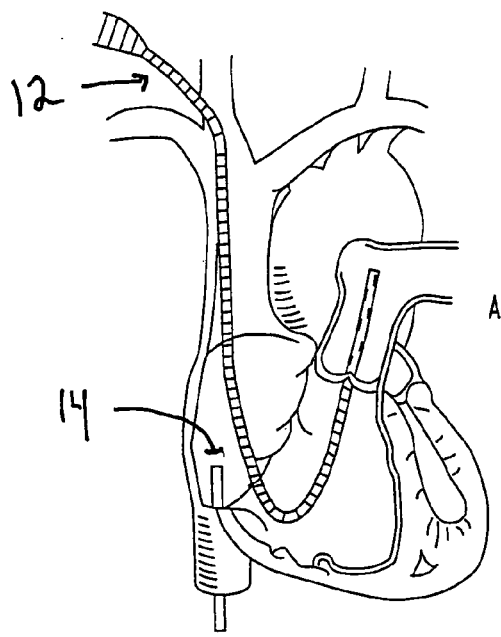
FIG. 8 is a schematic representation of the 21 Fr venous drainage cannula positioned in the right atrium and the 17 Fr return cannula in the main pulmonary artery.

Suggested Clinical Protocol for use of the TandemHeart for Right Heart Support:
1. PA cannulation:
   a. Use 18 ga. Percutaneous Entry Needle With Baseplate to access RIJ—
      1. Needle: Cook BSDN-18-9.0 (18 ga by 9 cm long) Quick reorder 002401.
   b. Place 0.035"×180 cm Guidewire through needle—advance about 15 cm into RIJ—FIG. 1
      2. Guidewire: Boston Scientific THSCF-35-180-15 (quick reorder 036363).
   c. Remove Needle. Needle may be saved for re-use.
   d. Dilate vessel with appropriate sized vessel dilator:
      i. Serially dilate as appropriate using 8 Fr dilator—Dilator may be saved for re-use—
         3. Dilator: Daig 405512.
      ii. Serially dilate as appropriate using 12 Fr Dilator—Dilator may be saved for re-use—
         4. Dilator: Daig 405528.
      iii. Serially dilate as appropriate using 16 Fr Dilator—Dilator may be saved for re-use—
         5. Dilator: Daig 405544.
   e. Insert 17 Fr Femoral Venous Cannula With Introducer over 0.035" Guidewire into SVC (or as far as RA)—(FIG. 2)—
      6. Cannula: Medtronic 96670-017.
   f. Remove 0.035" Guidewire first and then remove Introducer. Guidewire may be saved for re-use. FIG. 3 g. Place Pulmonary Wedge Pressure Catheter through 17 Fr Cannula—inflate balloon, and advance to PA (FIG. 4)—
  7. PW Catheter: Medtronic 7 Fr Pulmonary Wedge Pressure Catheter #150075.
h. Place 0.035" 180 cm Guidewire—(same Guidewire may be re-used)—through 7 Fr Catheter and advance to the tip of the Pulmonary Wedge Pressure Catheter. The Guidewire provides stiffness which allows the 17 Fr Cannula to be advanced—FIG. 5
  8. Guidewire: Boston Scientific THSCF-35-180-15 (quick reorder 036363)
i. Advance 17 Fr cannula (without introducer) over Pulmonary Wedge Pressure Catheter/Guidewire up to balloon (FIG. 6).
j. Deflate balloon and withdraw first Guidewire and then Pulmonary Wedge. Pressure Catheter, leaving 17 Fr Cannula alone in PA.
k. Cross-clamp Cannula to prevent blood loss.
l. Secure 17 Fr Cannula in place to prevent displacement out of the PA.

Figure 7:
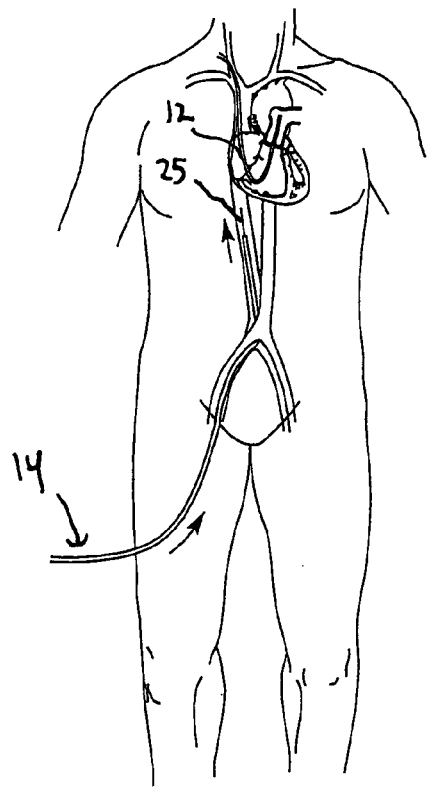
FIG. 7 is a schematic representation of the 21 Fr venous drainage cannula advanced from the femoral vein over a wire, using the Seldinger technique.

2. RA Cannulation:
a. Use 18 ga. Percutaneous Entry Needle With Baseplate to access RIJ—Same Needle may be reused—
  9. Needle: Cook BSDN-18-9.0 (18 ga by 9 cm long) Quick reorder 002401
b. Place 0.035"×180 cm Guidewire through Needle (same Guidewire may be re-used)—advance into RA—
  10. Guidewire: Boston Scientific THSCF-35-180-15 (quick reorder 036363).
c. Remove Needle.
d. Dilate vessel with appropriate sized vessel dilator:
  i. Serially dilate as appropriate using 8 Fr dilator—Dilator may be saved for re-use—
    11. Dilator: Daig 405512.
  ii. Serially dilate as appropriate using 12 Fr Dilator—Dilator may be saved for re-use—
    12. Dilator: Daig 405528.
  iii. Serially dilate as appropriate using 16 Fr Dilator—Dilator may be saved for re-use—
    13. Dilator: Daig 405544.
e. Insert 21 Fr TandemHeart THTC with Obturator over the Guidewire into the RA. (FIG. 7, 8)
f. Remove Guidewire first and then Obturator.
g. Cross-clamp 21 Fr Cannula to prevent blood loss.
h. Secure 21 Fr THTC in place.

3. Connect to TandemHeart Pump:
a. Connect 21 Fr Cannula to TandemHeart Pump inlet (blue striped tubing). Locate Pump on outside of patient's leg with Pump outlet pointed up toward the patient's head.
b. Prime pump by releasing cross-clamp from 21 Fr tubing and slowly filling and de-airing pump.
c. Connect 17 Fr cannula to TandemHeart pump outlet (red striped tubing). Use straight connector from TandemHeart Pump Kit and additional length of red stripe tubing as needed. Make final wet-to-wet connection, ensuring that the circuit has been completely de-aired—
  14. Tubing: CardiacAssist #2000-0313.
  Note: The pump and tubing may be pre-primed with Plasmalyte if desired to reduce patient volume loss. If the circuit is pre-primed, some hematocrit reduction will occur. The prime volume of the circuit is about 138 cc.

4. Initiate support:
a. Start pump at low speed.
b. Release cross-clamps.
c. Adjust speed to attain desired flow. Note: Caution should be taken not to over-drive the pump, which could result in excessive PA pressure.

Although the invention has been described in detail in the foregoing embodiments for the purpose of illustration, it is to be understood that such detail is solely for that purpose and that variations can be made therein by those skilled in the art without departing from the spirit and scope of the invention except as it may be described by the following claims.

What is claimed is:

1. A method for assisting the heart of a patient comprising the steps of:
inserting a pulmonary artery (PA) cannula into the right internal jugular vein of the patient;
moving the PA cannula in the vasculature and into the PA of the patient via an anatomical pathway through the right heart;
inserting a right atria (RA) cannula into the a peripheral vein of the patient;
moving the RA cannula in the vasculature and into the RA of the patient, so that the right ventricle of the patient is bypassed;
connecting the RA cannula and the PA cannula to a blood pump disposed outside of the patient, with the RA cannula connected to an inlet of the blood pump and the PA cannula connected to an outlet of the blood pump; and
activating the blood pump to provide only right ventricular assist to the heart of the patient and without open heart surgery or left ventricle support.

2. A method as described in claim 1 wherein the inserting the PA cannula step includes passing a pulmonary wedge pressure catheter through the PA cannula, floating the catheter into the pulmonary artery, and advancing a super stiff wire through a pulmonary artery port of a Swan-Ganz catheter.

3. A method as described in claim 2 further comprising removing the pulmonary wedge pressure catheter and the wire from the patient once the PA cannula is in the patient.

4. A method as described in claim 1 wherein the PA cannula has an end hole and at least two side holes which allow blood flow to the left and right lungs of the patient, without allowing backflow into the right ventricle of the patient.

5. A method as described in claim 1 wherein the inserting the RA cannula step includes inserting the RA cannula percutaneously into the patient.

6. A method as described in claim 1 further comprising pumping unoxygenated blood from the right atrium with the blood pump through the RA cannula and returning the blood to the pulmonary artery through the PA cannula.

7. A method as described in claim 6 further comprising controlling the blood pump with a controller in communication with the blood pump which detects and manages faults and produces an alert signal in response to a detected fault.

8. A method as described in claim 1 further comprising placing the blood pump in a holder that attaches to the lower body of the patient.

9. A method as described in claim 1 further comprising sewing the PA cannula and the RA cannula to the patient.

10. A method as described in claim 1 wherein the inserting the RA cannula step includes inserting the RA cannula into the peripheral vein of the patient over a wire.

11. A method as described in claim 10 further comprising advancing the RA cannula along the wire into the RA and removing the wire.

12. A method as described in claim 1 wherein the activating step includes starting 2 L/min blood flow for at least two minutes and then adjusting the blood flow based on the patient's requirements.

13. A method as described in claim 1 further comprising using imaging guidance when the RA cannula and the PA cannula are in the RA and PA, respectively.

14. A method as described in claim 1 wherein the activating step includes the step of providing blood flow to the right and left lungs through the PA cannula.

15. A method as described in claim 1 further comprising providing blood flow from the blood pump for right ventricular assist of the patient at a level which is ½ to ⅔ of normal cardiac blood flow of the patient.

16. A closed chest system for assisting the right heart of a patient comprising:
 a pulmonary artery (PA) cannula adapted for insertion into the right internal jugular vein of the patient and to extend into the PA of the patient via an anatomical pathway through the right heart;
 a percutaneous right atria (RA) cannula adapted for insertion into a peripheral vein of the patient and to extend into the RA of the patient, so that the right ventricle of the patient is bypassed; and
 a blood pump disposed outside of the patient, the blood pump comprising an inlet connected to the RA cannula and an outlet connected to the PA cannula for providing only right ventricular circulatory support to the patient without open heart surgery or left ventricle support.

17. A closed chest system as described in claim 16 wherein the pump is a ventricular assist pump.

18. A closed chest system as described in claim 17 wherein the PA cannula has an end hole and two side holes for blood flow to the right and left lungs.

19. A closed chest system as described in claim 16 further comprising a holder which holds the blood pump securely to the patient.

20. A closed chest system as described in claim 16 wherein the blood pump comprises a controller operating the blood pump to provide right ventricular assist of the patient at a level which is ½ to ⅔ of normal cardiac blood flow of the patient.

* * * * *

UNITED STATES PATENT AND TRADEMARK OFFICE
CERTIFICATE OF CORRECTION

PATENT NO. : 8,550,973 B2  
APPLICATION NO. : 11/328961  
DATED : October 8, 2013  
INVENTOR(S) : James A. Magovern et al.

Page 1 of 1

It is certified that error appears in the above-identified patent and that said Letters Patent is hereby corrected as shown below:

Title Page 2, Item 56, Column 2, Line 1, delete "Potentialies" and insert -- Potentialities --

In the Claims

Column 8, Line 21, Claim 1, before "peripheral" delete "the"

Signed and Sealed this  
Fourth Day of March, 2014

Michelle K. Lee  
*Deputy Director of the United States Patent and Trademark Office*